US006191168B1

(12) United States Patent
Rubenstein

(10) Patent No.: US 6,191,168 B1
(45) Date of Patent: Feb. 20, 2001

(54) METHODS FOR THE USE OF NONPROTEIN AMINO ACIDS AS THERAPEUTIC AGENTS

(75) Inventor: Edward Rubenstein, 5 Waverly Pl., Hillsborough, CA (US) 94010

(73) Assignee: Edward Rubenstein, Hillsborough, CA (US)

( * ) Notice: Under 35 U.S.C. 154(b), the term of this patent shall be extended for 0 days.

(21) Appl. No.: 09/324,181

(22) Filed: Jun. 1, 1999

Related U.S. Application Data

(60) Provisional application No. 60/087,746, filed on Jun. 2, 1998.

(51) Int. Cl.[7] ................................................. A61K 31/195
(52) U.S. Cl. ........................ 514/561; 514/210; 514/274; 514/419; 514/423; 514/315; 514/354; 514/538; 514/562; 514/563; 514/564; 514/565
(58) Field of Search ................................. 514/210, 564, 514/561, 565, 562, 419, 274, 423, 315, 354, 563, 538

(56) References Cited

U.S. PATENT DOCUMENTS

| 3,950,536 | * | 4/1976 | Barer et al. . |
|---|---|---|---|
| 4,481,219 | | 11/1984 | Watkinson . |
| 5,409,898 | | 4/1995 | Darveau et al. . |
| 5,458,876 | | 10/1995 | Monticello . |
| 5,650,320 | | 7/1997 | Caufield et al. . |

OTHER PUBLICATIONS

CA 93: 180253, Al Baldavi, 1978.*
CA 96: 173962, Smith et al, 1981.*
CA 120: 102294, Hodges et al, 1993.*
CA 115: 189747, Yu et al, 1991.*
CA 122: 29881, Lai et al, 1994.*
CA 126: 268319, Breton et al, 1997.*
Bell. (1958). "Canavanine and Related Compounds in Leguminosae," *Biochem J.* 70:617–619.
Bisby et al. (1994). *Phytochemical Dictionary of the Leguminose*, vol. 1–2. (Title page and table of contents only).
Butler et al. (1967). "Uptake and Metabolism of Inorganic Forms of Selenium–75 by *Spirodela Oligorrhiza*," *Aust. J. Biol. Sci.* 20:77–86.
Conn. (1981). "Secondary Plant Products" *The Biochemistry of Plants* vol. 7(Title page and table of contents only).
Cowie et al. (1957). "Biosynthesis by *Escherichia Coli* of Active Altered Proteins Containing Selenium Instead of Sulfur," *Biochem et Biophysica Acta.* 26:252–261.
Gennaro ed. (1995). *Remington: The Science and Practice The Science and of Pharmacy* (Title page and table of contents only).

(List continued on next page.)

Primary Examiner—Rebecca Cook
(74) *Attorney, Agent, or Firm*—Morrison & Foerster LLP

(57) ABSTRACT

Provided are compositions comprising nonprotein amino acids and modified amino acids, as well as methods for the use of nonprotein amino acids and modified amino acids in inhibiting the growth of infective agents. In one embodiment the compounds and compositions may be used for treating an infection in a human or animal. For example, infectious agents include resistant strains of Acinetobacter, Klebsiella, Serratia, *Staphylococcus aureus* and *Streptococcus pneumoniae*, vancomyocin-resistant enterococci and multi-drug resistant mycobacteria, and other emerging resistant organisms. The compounds and methods are useful for treating infections caused by organisms, including viral pathogens, fungi, yeast, helminths or protozoans. The nonprotein amino acids and modified amino acids may be administered by any route known in the air, such as parenterally, orally, by inhalation or topically, and optionally may be administered in a carrier, such as a polymeric carrier.

16 Claims, 1 Drawing Sheet

OTHER PUBLICATIONS

Green et al. (1983). "Enhancement of Human Tumor Cell Killing by L–Canavanine in Combination with γ–Radiation," *Cancer Res.* 43:4180–4182.

Hakoda et al. (1992). "Production and Biological Activities of a New Antifungal Antibiotic, Tan–950 A," *J. Antibiotics* 45:854–860.

Kruse et al. (1958). "The Competitive Effect of Canavanine on Utilization of Arginine in Growth of Walker Carcinosarcoma 256 Cells in Vitro," *Cancer Res.* 18:279–282.

Kydonieus ed. (1992). *Treatise on Controlled Drug Delivery* Princeton, New Jersey. (Title page and table of contents only).

Lee. (1992). Treatise on Controlled Drug Delivery. Kydonieus ed., Marcel Dekker, Inc.: New York., pp. 155–197.

Levy. (1998). "Multidrug Resistance—A Sign of the Times," *NewEng. J. Med.* 338:1376–1378.

March ed. (1985). *Advanced Organic Chemistry* Wiley–Insterscience Publication (Title page and table of contents only).

O'Hanley. (1996) *Scientific American Medicine*. Dale et al. ed., Scientific American, Inc., New York pp. 4–8.

Osborne et al. (1994). "The Magical and Medicinal Usage of *Stangeria eriopus* in South Africa," *J. Ethno.* 43:67–72.

Paris et al. (1995). "Unusual Transformation of the 3–Hydroxyl–Picolinoyl Residue of Pristinamycin IA," J. of Antibiotics 48:676–682.

Phung–Ba et al. (1995). "Interaction of Pristinamycin IA with P–Glycoprotein in Human Intestinal Epithelial Cells," *European J. Pharm.* 288:187–192.

Robinson ed. (1980). *The Organic Constituents of Higher Plants* Amherst, Mass: Corus Press, 1980. (Title page and table of contents only).

Ron et al. (1992). *Treatise on Controlled Drug Delivery* Kydonieus ed. Marcel Dekker, Inc.: New York, pp. 199–224.

Rosenthal et al. ed. (1979). "Naturally Occurring, Toxic Nonprotein Amino Acids" *Herbivores: Their Interaction with Secondary Plant Metabolites* Academic Press, pp. 361–363.

Rosenthal. (1977). "The Biological Effects and Mode of Action of $_L$–cavanine, A Structural Analogue of $_L$–arginine," *The Quarterly Review of Biology* 52:155–178.

Rubin. (1997). *Scientific American Medicine.* Scientific American, Inc., New York pp. 1–20.

Schenk et al. (1991). "β–(3–Isolaxazolin–5–On–2–YL)–Alanine From Pisum: Allelopathic Properties and Antimycotic Bioassay," *Phytochemistry* 30(2):467–470.

Simberkoff. (1994). "Drug–Resistant Pneumococcal Infections in the United States," *JAMA* 271:1875–1876.

Simon. (1997). *Scientific American Medicine.* Scientific American, Inc., New York pp. 7–26.

Swaffar et al. (1994). "Inhibition of the Growth of Human Pancreatic Cancer Cells by the Arginine Antimetabolite $_L$–Cavanine," *Cancer Res.* 54:6045–6048.

Thomas et al. (1986) "Growth Inhibition of a Rat Colon Tumor by L–Canavanine," *Cancer Res.* 46:2898–2903.

Wallsgrove ed. (1995) *Amino Acids and Their Derivatives In Higher Plants* Cambridge University Press (Title page and table of contents only).

Weitzman et al. (1996). "Dermatophytes Gross and Microscopic," *Dermatol. Clin.* 14(1):9–22.

Weller. (1998). *Scientific American Medicine.* Scientific American, Inc., New York pp. 1–18.

Wink (1997) "Special Nitrogen Metabolism" *Plant Biochemistry* Dey et al. ed. Academic Press, pp. 439–486, 1997.

Woods "Antibacterial Susceptibility Tests, Detection and Disc Diffusion Methods" *Manual of Clinical Microbiology* 6th Edition Murray et al ed. ASM Press: Washington D.C., pp. 1327–1341, 1995.

\* cited by examiner

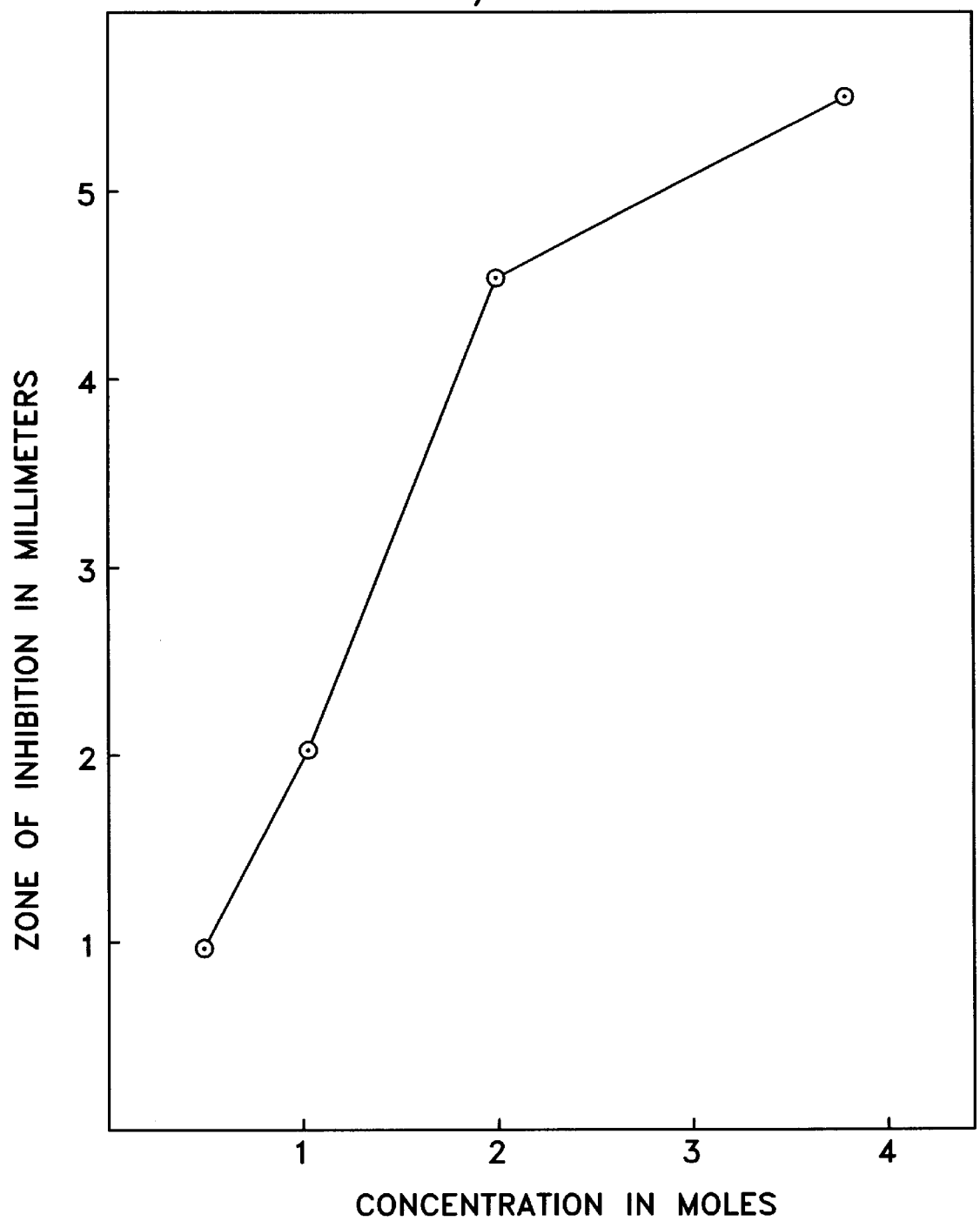

METHODS FOR THE USE OF NONPROTEIN AMINO ACIDS AS THERAPEUTIC AGENTS

CROSS REFERENCE TO RELATED APPLICATIONS

This application claims the benefit of U.S. Provisional Patent Application Ser. No. 60/087,746, filed Jun. 2, 1998, the disclosure of which is incorporated herein by reference in its entirety.

TECHNICAL FIELD

This invention relates to compositions comprising nonprotein amino acids, and methods for the use of nonprotein amino acids as anti-infective agents.

BACKGROUND ART

Plant and animal proteins generally include twenty "protein" amino acids: glycine, alanine, valine, leucine, isoleucine, lysine, phenylalanine, tryptophan, tyrosine, serine, threonine, cysteine, methionine, arginine, asparagine, aspartic acid, glutamine, glutamic acid, histidine, and proline. Hundreds of other "nonprotein" amino acids exist in nature. Most of the naturally occurring nonprotein amino acids are produced in plants, especially in seeds, in which their concentration may reach very high levels. Wink, M. "Special Nitrogen Metabolism," in *Plant Biochemistry*, Dey, P. M. and Harborne, J. B., Eds., Academic Press, San Diego, pp. 439–486, 1997; Bell, *Biochem. J.*, 70:617–619 (1958); and Rosenthal and Bell, "Naturally Occurring, Toxic Nonprotein Amino Acids," in *Herbivores: Their Interaction with Secondary Plant Metabolites*, Rosenthal and Janzen, Eds., Academic Press, New York, pp. 361–363, 1979.

Under normal circumstances, nonprotein amino acids are excluded from the process of protein synthesis in plants and animals. Some nonprotein amino acids, however, can be misincorporated into proteins. This can occur, for example, due to the failure of the ribosomal protein synthesizing mechanisms to discriminate between the nonprotein amino acid and one of the twenty protein amino acids. Such misincorporation has been shown to occur in various species, including bacteria, in which impaired colony growth may ensue. Cowie and Cohen, *Biochim. et Biophysica Acta*, 26:252–261 (1957); and Butler and Peterson, *Aust. J. Biol. Sci.* 20:77–86 (1967).

The nonprotein amino acid, canavanine, has been studied as an antineoplastic agent. Kruse and McCoy, *Cancer Res.*, 18:279–282 (1958); Green and Ward, *Cancer Res.*, 43:4180–4182 (1983); Thomas et al., *Cancer Res.*, 46:2898–2903 (1986); and Swaffar et al., *Cancer Res.*, 54:6045–6048 (1994). Canavanine also has been demonstrated to have potent antimetabolic, and in particular, insecticidal, properties. Rosenthal and Bell, "Naturally Occurring, Toxic Nonprotein Amino Acids," in *Herbivores: Their Interaction with Secondary Plant Metabolites*, Rosenthal and Janzen, Eds., Academic Press, New York, pp. 361–363, 1979.

DL methionine sulfoxide, delta-hydroxylysine hydrochloride, and aminoisobutyric acid have been used to suppress the growth of dry rot fungus and related fungi (*Armillaria mellea* and Basidiomycete) in the suppression of fungal timber infestation. U.S. Pat. No. 4,481,219, to the National Research Development Corporation. Beta-(3-isoxazolin-5-on-2-yl)-alanine has been shown to exhibit antimycotic activity towards *Saccharomyces cerevisiae*. Schenk et al., *Phytochemistry*, Oxford, Pergamon Press, 1991, v. 30(2), pp. 467–470. 2-Amino-3-(2,5-dihydro-5-oxo-4-isoxazolyl) propanoic acid has been reported to have antifungal activity against yeast including *Candida albicans* in vitro and in vivo in mice, and to have a low toxicity in mice. Hakoda et al., *J. Antibiotics*, 45:854–860 (1992).

While there have been a few isolated studies of certain activities of nonprotein amino acids, as well as studies identifying numerous different kinds of nonprotein amino acids in plants, for the most part, nonprotein amino acids, and in particular, methods for treating humans or animals therapeutically with nonprotein amino acids, have remained largely unexplored.

The emergence of resistant bacterial organisms poses a serious problem in infectious diseases, despite the availability of a large number of agents used for the prevention or treatment of bacterial infections. This is especially true in the hospital environment, in which outbreaks of highly resistant strains of Acinetobacter, Klebsiella, Serratia, and *Staphylococcus aureus*, among many others, pose a constant threat. H. Simon, "Antimicrobial chemotherapy," in *Scientific American Medicine*, Scientific American, Inc., Dale and Federman, Eds., New York, 7:XIV:11, June, 1997; and Levy, *N. Engl. J. Med.*, 338:1376–1378 (1998). The problem of resistance to antimicrobial agents extends to the larger community. Penicillin-resistant *Streptococcus pneumoniae* are an example. Simberkoff, *JAMA*, 271:1875–1876 (1994). The inevitability of resistance owing to microbial mutations results in the ongoing need for the development of antibacterial therapeutic agents.

Fungal infections remain a serious problem in the management of normal as well as immunologically impaired hosts. In the United States the principal systemic mycotic infections in immunologically competent individuals are histoplasmosis, coccidioimycosis and blastomycosis. A fourth infection, sporotrichosis, usually involves the skin and regional lymphatics, although systemic infection occasionally occurs. Fungal infections in the immunocompromised host have become a major problem because of the widespread use of therapeutic agents that damage the immune system, as in the chemotherapy of solid tumors, hematologic malignancies, autoimmune disease, and transplantation. Fungal infections are also a problem in a host immunocompromised as a result of a disorder, such as acquired immunodeficiency syndrome. The principal systemic or life-threatening fungal infections in immunocompromised hosts are: aspergillosis, candidiasis, cryptococcosis (torulosis), and mucormycosis (especially in individuals with diabetes). An additional infection in the immunocompromised now recognized to be fungal is that caused by *Pneumocystis carinii*.

Infections caused by dermatophytes or yeasts are treated with topical or oral agents. O'Hanley, "Fungal, Bacterial and Viral Infections of the Skin" in *Scientific American Medicine*, Scientific American, Inc., Dale and Federman, Eds., New York, 2:VII:4–8, April (1996). In the United States, the principal systemic mycotic infections in immunologically competent individuals are treated with amphotericin B. Rubin, R. H., "Infection in the Immunosuppressed Host," in *Scientific American Medicine*, Scientific American, Inc., Dale and Federman, Eds., New York, 7:X:1–20, January (1997). Systemically administered antifungal drugs are associated with severe side effects and dangerous toxicity. This is especially true for amphotericin B, the principal agent used in the treatment of serious infections. Although some antifungal agents have been developed, there remains a need for effective antifungal agents with minimal side effects.

Thus, there is a need for the development of compounds which are useful as anti-infective agents. There is a need for methods for treating humans and other animals with anti-infective agents which are effective against a wide variety of pathogenic infectious agents including bacteria, fungi, protozoa, and helminthic agents. There further is a need for compounds and compositions which can be administered via a variety of methods including topically, parenterally, orally, by inhalation and by implantation.

DISCLOSURE OF THE INVENTION

Methods and compositions for inhibiting growth of an infectious agent are provided. In one embodiment, a method is provided for inhibiting growth of an infectious agent comprising applying to the site of the infectious agent an effective amount of a nonprotein amino acid. Infectious agents include bacteria, such as Acinetobacter, Klebsiella, Serratia, *Staphylococcus aureus* and *Streptococcus pneumoniae,* vancomyocin-resistant enterococci and multi-drug resistant mycobacteria.

For example, the growth of gram positive bacteria, such as *Staphylococcus aureus,* may be inhibited by application of a nonprotein amino acid, such as 1-aminocyclopropane carboxylic acid or L-pyroglutamic acid. The growth of gram negative bacteria, such as *E. coli.,* may be inhibited by application of a nonprotein amino acid such as 1-aminocyclopropane carboxylic acid or L-pyroglutamic acid. The growth of yeast, such as *Saccharomyces cerevisiae* or *Candida albicans,* may be inhibited by application of a nonprotein amino acid such as L-α-amino-n-butyric acid; 2-amino-4-hydroxybutyric acid; L-azetidine-2-carboxylic acid; or 2-amino-3-ureido-propionic acid.

In another embodiment, a method of inhibiting growth of an infectious agent, such as a bacteria or yeast, is provided, the method comprising applying to the site of the infectious agent an effective amount of an amino acid ester, such as esters of L-phenylalanine, L-tryptophan and L-tyrosine. The esters may be, for example, alkyl esters, such as ethyl esters.

Compositions also are provided, comprising a nonprotein amino acid or an amino acid ester, and a carrier. The composition may be pharmaceutically acceptable. Exemplary carriers include oils, waxes, emulsifiers, alcohols, carboxyvinyl polymers, acrylic copolymers, polyacrylamides, polysaccharides, natural gums, clays, and fatty acids. In the composition, the nonprotein amino acid may be provided in an amount effective to inhibit the growth of an infectious agent.

Further provided are methods of treating an infection in a human or other animal, comprising administering to the human or other animal an effective amount of a nonprotein amino acid. In one embodiment, the nonprotein amino acid is administered to the subject in an effective amount for the treatment of an infection, including infections caused by resistant organisms, such as Acinetobacter, Klebsiella, Serratia, *Staphylococcus aureus, Streptococcus pneumoniae,* vancomyocin-resistant enterococci and multi-drug resistant mycobacteria.

The nonprotein amino acid may be administered to the human or animal in an effective amount for the treatment of a fungal infection, such as a fungal infection caused by *Histoplasma capsulatum, Coccidioides immitis, Blastomycoses dermatitidis,* Aspergillus, *Cryptococcus neoformans,* Phycomycetes, *Pneumocystis carinii,* Trichophylon, Microsporum, Epidermophyton, Candida and Malassezia. The nonprotein amino acid also may be administered for the treatment of an infection caused by other organisms, including a helminth or a protozoan. In another embodiment, the nonprotein amino acid is administered to the human or animal in an effective amount for the treatment of a viral infection, such as those caused by herpesviruses, enteric viruses, enteroviruses, retroviruses and hepatitis viruses.

The nonprotein amino acid may be administered by any route known in the art, such as parenterally, orally, by inhalation or topically. Optionally, the nonprotein amino acid may be administered in a carrier. For example, a topical fungal infection in a human may be treated by administering an effective antifungal amount of a nonprotein amino acid topically to the skin in a pharmaceutically acceptable carrier.

In one embodiment; the nonprotein amino acid is L-azetidine-2-carboxylic acid; 2-amino-4-(aminoxy) butanoic acid; 2-aminobutanoic acid; 2-aminohexanedioic acid; 2-amino-4-hydroxybutanoic acid; L-α-amino-n-butyric acid; 2-amino-4-hydroxybutyric acid; 2-amino-5-hydroxypentanoic acid; 2-amino-4-methyleneglutaric acid; 2-amino-4-methylenepentanedioic acid; 0-[(aminoiminomethyl)amino]homoserine; 2,5-diamino-4-hydroxypentanoic acid; N-(carboxyacetyl)alanine; [(2-amino-2-carboxyethyl) thio]succinic acid; 2,3-diaminopropanoic acid; $N^6$-(aminoiminomethyl) lysine, 2-amino-5-guanidino-4-hydroxypentanoic acid; $N^6$-(aminoiminomethyl)-4-hydroxylysine; N-(1H-indol-3-ylacetyl) aspartic acid; β-(2,4-dihydroxy-3-pyrimidinyl) alanine; 5-oxo-2-pyrrolidinecarboxylic acid; 2-piperidinecarboxylic acid; N-methylaminoacetic acid; 1,2, 3,6-tetrahydro-2-pyridinecarboxylic acid; α-amino-β-uracil-1-ylpropanoic acid; N-carboxyacetyl-D-phenylalanine; (+)-threo-1-amino-3-methylpentanoic acid; 4-hydroxymethyl-2-pyrrolidinecarboxylic acid; 5-hydroxy-2-piperidinecarboxylic acid; 1-amino-cyclopropane-1-carboxylic acid; or 2-amino-3-ureido-propionic acid or a combination thereof.

Preferred are nonprotein amino acids that substantially are non-toxic to humans, such as nonprotein amino acids found in plants that are commonly eaten by humans.

BRIEF DESCRIPTION OF THE FIGURE

FIG. 1 is a graph showing the concentration dependent inhibition of growth of *Staphylococcus aureus* by L-pyroglutamic acid.

MODES FOR CARRYING OUT THE INVENTION

Nonprotein amino acids which are useful as anti-infective agents are provided, as well as methods for their use. Methods are provided for the use of nonprotein amino acids as anti-infective agents, including antibacterial, antifungal, antiprotozoal, and antihelminthic agents. The nonprotein amino acids also are suitable for use in the treatment of infestations caused by mites, lice, and other ectoparasites. The nonprotein amino acids can be administered via a variety of methods including topically, intravenously, orally, by inhalation and by implantation.

Nonprotein Amino Acids

Plant and animal proteins generally are synthesized in vivo by using the same complement of twenty L-amino acids: glycine, alanine, valine, leucine, isoleucine, lysine, phenylalanine, tryptophan, tyrosine, serine, threonine, cysteine, methionine, arginine, asparagine, aspartic acid, glutamine, glutamic acid, histidine, and proline, which are referred to herein as "protein amino acids," since they commonly occur in both plant and animal proteins. In contrast, "nonprotein amino acids," as used herein, refers to amino acids other than the 20 protein amino acids. The nonprotein amino acid includes at least one amino group or amino group and at least one carboxyl group.

A large number of various nonprotein amino acids are available which exist in nature. Most of the naturally occurring nonprotein amino acids are produced in plants, especially in seeds, in which their concentration may reach very high levels. They are derived biosynthetically in plants from protein amino acids or from other biosynthetic routes. Nonprotein amino acids includes amino acids that are modified intracellularly after their incorporation into proteins.

The nonprotein amino acids may be, for example, formyl methionine that block aminopeptidases. Other examples of nonprotein amino acids include L-α-amino-n-butyric acid and L-homoserine (2-amino-4-hydroxybutyric acid).

The nonprotein amino acid may include a carbocyclic or heterocyclic ring, such as 1-aminocyclopropane carboxylic acid.

Exemplary nonprotein amino acids include: 3-cyanoalanine, canaline, S-aminoethylcysteine, L-azetidine-2-carboxylic acid, albizziine, Se-methylselenocysteine, L-canavanine, and L-indospicine, which are derived from L-cysteine and L-asparagine. Some of these, including L-indospicine and L-canavanine, are potentially toxic, for example, when ingested, and therefore may be used only if the toxic effect is limited, for example, by lowering the concentration, or by administering them topically. Wink, M. "Special Nitrogen Metabolism," in *Plant Biochemistry,* Dey, P. M. and Harborne, J. B., Eds., Academic Press, San Diego, pp. 439–486, 1997; Bell, *Biochem. J.,* 70:617–619 (1958); and Rosenthal and Bell, "Naturally Occurring, Toxic Nonprotein Amino Acids," in *Herbivores. Their Interaction with Secondary Plant Metabolites,* Rosenthal and Janzen, Eds., Academic Press, New York, pp. 361–363, 1979, the disclosures of which are incorporated herein.

Nonprotein amino acids are described extensively in the *Phytochemical Dictionary of the Leguminose,* International Legume Database Information Service and Chapman & Hall Chemical Database, Bisby et al, Eds., Vols. 1 and 2, Chapman & Hall, London, 1994; *The Biochemistry of Plants, Vol. 7,* "Secondary Plant Products", Conn, Ed., Academic Press, New York, 1981; Robinson, *The Organic Constituents of Higher Plants,* Cordus Press, 1980; *Herbivores. Their Interaction with Secondary Plant Metabolites,* Rosenthal and Janzen, Eds., Academic Press, New York, 1979; and *Amino Acids and Their Derivatives In Higher Plants,* Wallsgrove, Ed., Cambridge University Press, Cambridge, 1995, the disclosures of which are incorporated herein.

Many other nonprotein amino acids have been made synthetically, or can be made using synthetic organic chemistry techniques, as described, for example, in March, "Advanced Organic Chemistry", John Wiley & Sons, New York, 1985. Many others are readily available commercially.

A list of some nonprotein amino acids found in plants is shown below in Table 1. Many of these are available from Sigma, St. Louis, Mo., Aldrich, Milwaukee, Wis., Fluka, Ronkonkoma, N.Y.

TABLE 1

Nonprotein Amino Acids

| No. | Chemical name |
|---|---|
| 1 | 2-Amino-4-(aminoxy) butanoic acid |
| 2 | 2-Aminobutanoic acid |
| 3 | 2-Aminohexanedioic acid |
| 4 | 2-Amino-4-hydroxybutanoic acid |
| 5 | 2-Amino-5-hydroxypentanoic acid |
| 6 | 2-Amino-4-methyleneglutaric acid |
| 7 | 2-Amino-4-methylenepentanedioic acid |
| 8 | 0-[(Aminoiminomethyl) amino] homoserine |
| 9 | 2,5-Diamino-4-hydroxypentanoic acid |
| 10 | N-(Carboxyacetyl) alanine |
| 11 | [(2-Amino-2-carboxyethyl) thio] succinic acid |
| 12 | 2,3-Diaminopropanoic acid |
| 13 | $N^6$-(Aminoiminomethyl) lysine |
| 14 | 2-Amino-5-guanidino-4-hydroxypentanoic acid |
| 15 | $N^6$-(Aminoiminomethyl)-4-hydroxylysine |
| 16 | N-(1H-Indol-3-ylacetyl) aspartic acid |
| 17 | β-(2,4-Dihydroxy-3-pyrimidinyl) alanine |
| 18 | 5-Oxo-2-pyrrolidinecarboxylic acid |
| 19 | 2-Piperidinecarboxylic acid |
| 20 | N-methylaminoacetic acid |
| 21 | 1,2,3,6-Tetrahydro-2-pyridinecarboxylic acid |
| 22 | α-Amino-β-uracil-1-ylpropanoic acid |
| 23 | N-Carboxyacetyl-D-phenylalanine |
| 24 | (+)-threo-1-amino-3-methylpentanoic acid |
| 25 | 4-Hydroxymethyl-2-pyrrolidinecarboxylic acid |
| 26 | 5-Hydroxy-2-piperidinecarboxylic acid |
| 27 | 1-Amino-cyclopropane-1-carboxylic acid |

Other exemplary nonprotein amino acids, available from Sigma, are shown in Table 2 below.

TABLE 2

Nonprotein Amino Acids

| No. | Chemical name |
|---|---|
| 1 | 2-Amino-3-(4-aminophenyl) propanoic acid |
| 2 | 2-Amino-3-butenoic acid (Vinylglycine) |
| 3 | 2-Amino-3-cyanopropanoic acid |
| 4 | 1-Amino-1,3-cyclobutanedicarboxylic acid |
| 5 | 1-Aminocyclopropane carboxylic acid |
| 6 | 2-Amino-6-diazo-5-oxohexanoic acid |
| 7 | 2-Amino-3-(3,5-dibromo-4-hydroxyphenyl) propanoic acid |
| 8 | 3-Aminodihydro-2(3H)-furanone (Homoserine lactone) |
| 9 | 2-Amino-3-(3,4-dihydroxyphenyl) propanoic acid (3-Hydroxytyrosine) |
| 10 | 2-Amino-3,3-dimethylbutanoic acid |
| 11 | 2-Amino-1,1,2-ethanetricarboxylic acid |
| 12 | 2-Aminopheptanedioic acid |
| 13 | O-Oxalylhomoserine |
| 14 | 2-Amino-4-pentenoic acid |
| 15 | 2-Amino-2-phenylacetic acide |
| 16 | 2-Amino-3-phosphononpropanoic acid |
| 17 | 3-Amino-1,1,3-propanetricarboxylic acid |
| 18 | 5-(2-Carboxyethyl) cysteine |
| 19 | 2-3-Diaminobutanedioic acid |
| 20 | Guanidinoacetic acid (N-(Aminoiminomethyl) glycine) |
| 21 | 2,6-Pyridinedicarboxylic acid |
| 22 | S-Sulfocysteine |
| 23 | 6-N-Trimethyllysine betainee |

Modified Amino Acids

Modified amino acids also may be used in the applications for and compositions comprising nonprotein amino acids disclosed herein. For example, modified amino acids may be modified amino acids that are formed intracellularly. Modified amino acids in one embodiment are esters of nonprotein or the twenty protein amino acids. The amino acid esters can include alkyl esters such as methyl, ethyl, propyl, isopropyl, butyl and isobutyl esters. The esters may be naturally occurring or formed using synthetic methods available in the art. Examples of amino acid esters include esters of L-phenylalanine, L-tryptophan, and L-tyrosine, such as L-phenylalanine ethyl ester, L-tryptophan ethyl ester, and L-tyrosine ethyl ester, which are commercially available from Sigma (St. Louis, Mo.). Other modified amino acids include acetylates of various amino acids including the twenty protein amino acids.

Therapeutic Applications

The nonprotein amino acids and modified amino acids may be used in a variety of therapeutic applications. In one preferred embodiment, the nonprotein amino acids may be used in the treatment of infections caused by infectious organisms or other infectious agents. Nonprotein amino acids also can be used as antineoplastic agents, for example, in the treatment of solid and hematologic neoplasms.

As used herein, "infectious agents" include agents capable of growth, including unicellular microorganisms, such as bacteria, and yeast, or molecular infectious agents capable of reproducing, such as viruses and prions, as well as multicellular organisms such as helminths.

The nonprotein amino acids or modified amino acids may be used to treat an infection in an animal or human by administering an effective amount of the compound. An "effective amount" is an amount sufficient to effect beneficial or desired results, such as clinical results. For example, an "effective amount" may be an amount that is sufficient to palliate, ameliorate, stabilize, reverse, slow or delay the progression of a disease state.

As used herein, "treatment" is an approach for obtaining beneficial or desired clinical results, including, but not limited to, alleviation of symptoms, diminishment of extent of disease, stabilizing (i.e., not worsening) state of disease, preventing spread of disease, delay or slowing of disease progression, amelioration or palliation of the disease state.

Anti-infective nonprotein amino acids or modified amino acids may be employed that selectively interfere with the metabolism of the infectious agent with minimal impact on the host. The anti-infective properties of the nonprotein amino acid may result, for example, from misincorporation of the nonproteins amino acids into the proteins of the infectious agents. This can occur, for example, due to the failure of the ribosomal protein-synthesizing mechanisms to discriminate between the nonprotein amino acid and one of the twenty protein amino acids. Compounds are selected, in one embodiment, by culturing of the infectious agent, such as a bacteria, in the presence of the compound to select for those compounds which most severely impair growth and reproduction of the infectious agent. Preferred are nonprotein amino acids or modified amino acids that interfere with the infectious agent, e.g., by misincorporation into the proteins of the injecting organism, or by other toxic effects, and then cause deleterious consequences, but substantially are not misincorporated deleteriously into the proteins of the infected host or otherwise interfere with the infected host. Also preferred are those compounds which have the fewest and mildest side effects on the host. The nonprotein amino acids or modified amino acids may be administered singly or in combination.

In the embodiment wherein the nonprotein amino acid or modified amino acid is used as an anti-neoplastic agent, nonprotein acids are selected that inhibit proliferation or survival of malignant cells, while substantially not affecting the host, for example by misincorporation of the nonprotein amino acid in the malignant cell as a result of a genetic mutation that alters proteins involved in protein synthesis mechanisms in the malignant cell.

Nonprotein amino acids or modified amino acids may be selected for different therapeutic applications or routes of administration which have selected properties such as hydrophobicity, hydrophilicity, or pKa. For example, hydrophobic nonprotein amino acids are useful for the topical treatment of skin where adsorption is desired, or where hydrophobicity enhances penetration of the amino acid into the infectious organism. Conversely, hydrophilic amino acids may be used for topical treatment wherein minimal or no absorption into the skin or mucous membranes is preferred, for example, in the case wherein it is preferred to avoid systemic absorption of the amino acid due to possible systemic toxicity.

The nonprotein amino acids or modified amino acids may be directly administered at the site where treatment is needed, for example, parenterally or topically. For example, the compounds may be applied at the site where treatment is needed, such as the site of infection. In one embodiment, the compound is applied topically to skin for the treatment of a variety of skin lesions, in which inhibition of cell growth or destruction of lesions is required. Nonprotein amino acids and modified amino acids are suitable for treatment of humans, and also for veterinary use in the treatment of diseases of animals, including dogs, pigs, cows, cats, sheep, chickens and other birds, goats, and horses.

In one embodiment, nonprotein amino acids or modified amino acids are used in the treatment of bacterial infections, including those caused by resistant strains of Acinetobacter, Klebsiella, Serratia, *Staphylococcus aureus* and *Streptococcus pneumoniae,* as well as vancomyocin-resistant enterococci, multi-drug resistant mycobacteria, methicillin resistant Staphylococcus and other organisms that emerge and that are resistant to available antimicrobial agents. As used herein the term "resistant bacteria" or "resistant organism" refers to a bacteria or organism that has developed resistance to one or more therapeutic agents which has been used in the treatment of infection caused by the bacteria or other organism.

Nonprotein amino acids and modified amino acids also may be used in the treatment or prevention of infections caused by organisms such as Chlamydia, Mycoplasma, and Rickettsia.

In another embodiment, nonprotein amino acids or modified amino acids may be used for the treatment of fungal infections. Infections caused by dermatophytes or yeasts may be treated locally or systemically. Mycotic infections which may be treated include systemic mycotic infections in immunologically competent individuals, including histoplasmosis, coccidioimycosis and blastomycosis, as well as sporotrichosis, which usually involves the skin and regional lymphatics, although systemic infection occasionally occurs. Fungal infections in the immunocompromised host also may be treated. These may occur, for example, due to the use of therapeutic agents that damage the immune system, as in the chemotherapy of solid tumors, hematologic malignancies, autoimmune disease, in transplantation, and in other disorders. Fungal infections in immunocompromised hosts also may occur due to a disorder such as acquired immunodeficiency syndrome. Exemplary fungal infections in immunocompromised hosts which may be treated include aspergillosis, candidiasis, cryptococcosis (torulosis), and mucormycosis (especially in individuals with diabetes), as well as infection caused by *Pneumocystis carinii.*

Less serious but far more prevalent fungal infections also may be treated that infect the skin, hair and nails, such as the dermatophytoses, caused by species of Trichophyton, Microsporum, and Epidermophyton. The clinical syndromes caused by these species are those of tinea capitis (ringworm of the scalp), tinea corporis (ringworm of the glabrous or non-hair-bearing skin), tinea cruris (ring worm of the groin), tinea pedis (ringworm of the feet or athlete's foot), and tinea unguium, tinea of the nails. Weitzman and Pahye, *Dermatol. Clin.*, 14:9–22 (1996). Yeast infections may be treated that involve the skin and mucous membranes, such as those of the mouth and vagina, caused by Candida species and Malassezia species (also termed Pityrosporum).

Viral infections also may be treated including herpesviruses, such as HSV I, HSV II, varicella-zoster, cytomegalovirus, Epstein Barr virus and human herpesviruses 6, 7 and 8. Enteric viruses may be treated including rotavirus, Norwalk and related viruses. Enteroviruses may be treated including Coxsackieviruses. Viruses may be treated that cause diseases such as mumps, measles, rubella, roseola infantum, smallpox, vaccinia, molluscum contagiousum, paravaccinia, orf and monkeypox. Viral zoonoses may be treated including rabies, dengue, yellow fever, Rift Valley fever, hanta-virus pulmonary syndrome and related disorders, Ebola, Marburg, Crimean-Congo, hemorrhagic fever, monkey-B, Newcastle, vesicular stomatitis, and foot and mouth viruses. Slow viruses may be treated including prion diseases such as kuru, and Creutzfeldt-Jakob. Retroviruses may be treated, including HIV-1 and 2, and HTLV-I and II. Additionally hepatitis viruses, such as hepatitis A, B, C, D, and E may be treated. Additionally, other viruses may be treated including parvovirus, papovavirus, adenoviruses, coronavirus, influenza viruses such as influenza A and B, parainfluenza, respiratory syncytial virus and rhinoviruses.

The nonprotein amino acids can also be used for the prevention and treatment of infections caused by helminthic parasites, including roundworms, tapeworms and flukes. Exemplary helminths include trichinellas. Nematodes that cause intestinal infections may be treated including roundworm, pinworm, hookworm, whipworm, and *Strongyloides stercoralis*. Nematodes that cause tissue infections may be treated, such as those that cause anisakiasis; visceral larva migrans; toxocara canis; angiostrongylus; mammomonogamosis; gnathostomiasis; dracunculiasis; and filariasis. Trematode infections may be treated including schistosomiasis; paragonimiasis; clonorchiasis; opisthorchiasis; fascioliasis; fasciolopsiasis; and well as diseases caused by other small intestinal flukes, such as Metagonimus and Heterophyes. Cestode infections may be treated, such as those caused by fish tapeworm, pork tapeworm, beef tapeworm, and dwarf tapeworm. Other helminthic diseases which may be treated include hydatid disease. Helminthic infections may be treated as described, for example, in Weller, "Helminthic Infections" in *Scientific American Medicine*, Scientific American, Inc., Dale and Federman, Eds., New York, 7:XXXV:1–18 (1998), the disclosure of which is incorporated herein.

The nonprotein amino acids can also be effective for the prevention and treatment of protozoal infections, including but not limited to the following: toxoplasmosis; malaria; babesiosis; giardiasis; amebiasis; coccidiosis; isosporiasis; cryptosporidiosis; cyclosporiasis; sarcospordiosis, balantidiasis; infection caused by *Dientamoeba fragilis*; infection caused by *Blastocystis hominis*; microsporidiosis; infections due to free-living amebae; leishmaniasis; American trypanosomiasis; and African trypanosomiasis. The nonprotein amino acids can also be used for the treatment of cutaneous infestations caused by other ectoparasites, such as scabies, pediculosis, myiasis, seabather's eruption, swimmer's itch, and flea infestations.

Whereas any of a variety of nonprotein amino acids may be used in the treatments described above, some preferred nonprotein amino acids are those listed in Table 1.

Carriers and Routes of Administration

The nonprotein amino acid or modified amino acid, optionally in a carrier, may be administered by a variety of routes known in the art including topical, oral, parenteral (including intravenous, intraperitoneal, intramuscular and subcutaneous injection as well as intranasal or inhalation administration) and implantation. The nonprotein amino acid further may be injected into a body cavity or subarachnoid space, or be infused to a hollow organ or structure, such as a ureter or bile duct. Nonprotein amino acids that are nonabsorbable across the skin or mucous membranes are especially suitable for topical use. The nonprotein amino acids may be administered to humans as well as to animals for veterinary purposes, such as a dog, pig, cow, cat, sheep, fowl, or a horse.

The nonprotein amino acid or modified amino acid, or mixtures thereof, may be provided in pharmaceutically acceptable form, and may be provided in a variety of carriers, including a range of pharmaceutically acceptable carriers available in the art. The carriers may include, for example, diluents, solvents, buffers, solubilizers, suspending agents, viscosity controlling agents, binders, lubricants and stabilizers, sugars, amino acids, and electrolytes. The nonprotein amino acid or modified amino acid also may be provided in a polymeric carrier, such as a polyester, polyanhydride, or polyamide. The nonprotein amino acid may be provided in a carrier suitable for the particular route of administration selected including topical, oral, parenteral (including intravenous, intraperitoneal, intramuscular and subcutaneous injection as well as intranasal or inhalation administration) and implantation, as described in the art, for example, in "Remington: The Science and Practice of Pharmacy", Mack Publishing Company, Pennsylvania, 1995, the disclosure of which is incorporated herein by reference.

Controlled release systems also may be used, as described for example in: Lee, "Diffusion-Controlled Matrix Systems", pp. 155–198 and Ron and Langer, "Erodible Systems", pp. 199–224, in "Treatise on Controlled Drug Delivery", A. Kydonieus Ed., Marcel Dekker, Inc., New York 1992, the disclosures of which are incorporated herein.

Other Applications

The nonprotein amino acids and modified amino acids also may be used in other applications to inhibit or prevent the growth of microbial organisms. For example, the compounds may be provided in a number of materials including skin creams and lotions for topical application, or in soaps and detergent formulations, to enhance the antimicrobial properties of the material to which is added. The compounds may be provided in carriers such as water in a variety of forms, such as an aerosol suitable for a variety of antimicrobial uses.

The compounds may be in the form of aqueous, alcoholic or aqueous-alcoholic solutions, or in the form of creams, gels, emulsions or foams. The compounds may be provided in compositions in the form, for example, of an aqueous, aqueous-alcoholic or oily solution, or of an oily suspension, or of a dispersion of the lotion or serum type, of emulsions of liquid or semi-liquid consistency of the milk type, which are obtained by dispersing a fatty phase in an aqueous phase (O/W) or, conversely, (W/O), or of suspensions or emulsions of soft consistency of the cream type or of aqueous or anhydrous gels, of micro-emulsions or, alternatively, microcapsules or microparticles, or of vesicular dispersions of the ionic and/or nonionic type. These compositions are formulated via techniques known in the art.

The compounds may be provided in compositions constituting, for example, cleansing, protecting, treatment or care creams for the face, for the hands, for the feet, for large anatomical folds or for the body (for example day creams, night creams, makeup removing creams, foundation creams, antisun or sunscreen creams), fluid foundations, makeup removing milks, body protecting or care milks, aftersun milks, lotions, gels or foams for skin care, such as cleansing lotions, aftersun lotions, artificial tanning lotions, bath compositions, deodorant compositions, aftershave gels or lotions, depilatory creams, compositions against insect bites, anti-pain compositions, compositions for treating certain skin diseases such as eczema, rosasea, psoriasis, lichens, severe pruritus and those indicated above.

The compositions may also comprise solid preparations, e.g., cleansing bars or soaps. The compositions may also be packaged in the form of an aerosol composition, also comprising a pressurized propellant agent.

The compounds may also be incorporated into various compositions for hair care, and including shampoos, hair-setting lotions, treatment lotions, hair-styling creams or gels, dye compositions, lotions or gels for preventing hair loss, antiparasitic shampoos and the like.

The compositions may also be provided in a form suitable for dentibuccal or oral use, for example a toothpaste. In this case, the compositions may contain customary additives for compositions suited for oral use, such as surface-active agents, thickening agents, humectants, polishing agents such as silica, various active ingredients such as fluorides, and optionally sweeteners such as sodium saccharinate.

The compounds may be provided in compositions including oils, waxes, emulsifiers and coemulsifiers and lipid vesicles. The compositions may contain additives normally used in the field, such as hydrophilic or lipophilic gelling agents, hydrophilic or lipophilic additives, preservatives, antioxidants, solvents, perfumes, fillers, sunscreens, odor absorbers and colorants.

Exemplary oils or waxes include mineral oils, vegetable oils (such as soya bean oil, palm oil, liquid fraction of shea butter, sunflower oil), animal oils (e.g., perhydrosqualene), synthetic oils, silicone oils or waxes (e.g., cyclomethicone, dimethicone) and fluorinated oils (e.g., perfluoropolyethers). Fatty alcohols (e.g., cetyl alcohol), fatty acids (e.g., stearic acid) and waxes (e.g., beeswax, carnauba wax and paraffin wax) may be provided, e.g. by adding to these oils.

Any of a variety of carriers including emulsifiers, waxes, oils, solvents, gelling agents and the like may be included in the compositions. Exemplary emulsifiers include glycerol stearate, PEG-100 stearate, polyglyceryl-3 hydroxylauryl ether and polysorbate 60. Exemplary solvents include alcohols, such as ethanol and isopropanol, and propyleneglycol. Exemplary hydrophilic gelling agents include carboxyvinyl polymers (carbomer), acrylic copolymers such as acrylate/alkylacrylate copolymers, polyacrylamides, polysaccharides such as hydroxypropyl-cellulose, natural gums and clays. Exemplary lipophilic gelling agents include modified clays such as bentones, metallic salts of fatty acids such as aluminum stearates and hydrophobic silica, ethyl cellulose, and polyethylene.

The compositions may contain other hydrophilic active agents, such as proteins or protein hydrolysates, protein amino acids, polyols, urea, allantoin, sugars and sugar derivatives, water-soluble vitamins, vegetable or bacteria extracts and starch. Representative lipophilic active agents include retinol (vitamin A) and derivatives thereof, tocopherol (vitamin E) and derivatives thereof, essential fatty acids, ceramides, and essential oils.

The compositions containing nonprotein amino acids and modified amino acids also may further contain other agents. such as anti-free radical agents such as alpha-tocopherol or esters thereof, superoxide dismutases, and certain metal chelators or ascorbic acid and esters thereof, anti-dandruff agents such as octopirox or zinc pyrithione; or antiacne agents such as retinoic acid or benzoyl peroxide. Other agents include betahydroxy acids (such as salicylic acid and its derivatives), alpha.-keto acids, beta-keto acids, retinoids (such as retinol, retinal retinoid acid), anthralins (such as dioxyanthranol), anthranoids, peroxides (e.g. of benzoyl), minoxidil, lithium salts, antimetabolites, vitamin D and derivatives thereof, hair dyes or colorants (such as para-phenylenediamine and derivatives thereof, and aminophenols), perfuming alcoholic solutions (such as perfumes, toilet water, aftershave, and deodorants), antiperspirants (such as certain aluminum salts), depilatory or permanent-waving active agents (such as thiols), or depigmenting active agents (such as hydroquinone).

Such compositions may be used in various hygienic, cosmetic or pharmaceutical applications, such as application of creams, gels, serums, lotions, makeup removing milks or aftersun or sunscreen compositions onto the skin or onto dry hair, application of a hair lotion onto wet hair, of shampoos, or application of toothpaste onto the gums.

Compositions, such as forms of gels, ointments or creams, may include one or more materials such as water, mineral oil, a lower alcohol, a mono or polyglycol (e.g., ethylene glycol, propylene glycol; polyethylene glycol; polyoxyalkylene derivatives of propylene glycol), a fatty acid ester (e.g., any of the well known alkyl stearates, oleates and linoleates) or other organic compounds or polymers (such as dimethylsulfoxide, dimethylformamide, dimethylacetamide, 1,2,6-hexanetriol, butanediol). The carrier may include materials such as nonionic polyalkylene derivatives of propylene glycol sold under the trademark "Pluronic" from Wyandotte Chemicals Corp. These polyglycols have molecular weights in the range of 1,000 to >15,000 and are available in solid or liquid forms, and can be mixed with each other or combined with water or organic liquids so that those skilled in the art can readily obtain the degree of viscosity desired. Control of the degree of viscosity can also be accomplished by the use of gelling agents such as hydroxypropyl cellulose, hydroxyethyl cellulose, carbonaceous polymers, and combinations thereof.

For example, an ointment, cream or paste form (water immiscible or water miscible) may be formed by heating white petrolatum in a suitable container (glass-lined or stainless steel) until fluid and adding the active ingredients in the form of a suspension, a finely powdered, micronized state, or solubilized in a suitable solvent system. Suitable oil soluble surfactants (e.g., hydroxylated lanolin, ethoxylated lanolin derivatives or polyoxyethylene esters) can be added to the petrolatum to make the preparation water miscible, or the surfactants may be omitted to make the ointment water-immiscible. The method of preparation, dissolving the solid ingredients in the primary carrier using a suitable container (glass or stainless steel lined) and mixers, with filtration and viscosity adjustment as necessary, is well known.

The invention will be further understood by the following non-limiting examples.

EXAMPLES

Example 1
Inhibition of Microbial Growth

The ability of a variety of nonprotein amino acids and amino acid esters to inhibit microbial growth was assessed. The following organisms were tested: *Escherichia coli* (ATCC 25922); *Staphylococcus aureus* (ATCC 25923); *Saccharomyces cerevisiae* (BY 4743); and *Candida albicans*. The nonprotein amino acids and derivatives were obtained from Sigma (St. Louis, Mo.).

For assessing inhibition of bacterial growth, the Kirby/Bauer disc diffusion method was used. Woods, G. L., Washington, J. A., "Antibacterial Susceptability Tests, Detection and Disc Diffusion Methods," in *Manual of Clinical Microbiology*, Murray, P. R. et al., ASM Press, Washington, D.C., 1995, 6th Edition, pp. 1327–1341. The organisms were subcultured 24 hours before testing. A single colony was transferred via a sterile cotton tip into 10 ml sterile capped test tube, containing Mueller-Hinton Broth (5.47 mg $Ca^{++}$/L, 4.03 mg $Mg^{++}$/L in Mueller-Hinton Broth, Beckton Dickenson (Sparks, Md.), dry powder). The suspension was mixed with a vortexer for 15 sec. The concentration was adjusted using a McFarland Equivalence Turbidity Standard, 0.5 Remel (Lenexa, Kans.). Thereafter the organisms were inoculated on an agar plate by streaking in three planes, incubated at 35° C. for 24 hours, and then read.

*Escherichia coli* were grown on Mueller II Agar (Becton-Dickinson), and *Staphylococcus aureus* were grown on Mueller-Hinton agar containing 5% sheep blood (Becton-Dickinson).

The yeasts, *Saccharomyces cerevisiae*, and *Candida albicans*, were grown overnight in liquid YPD medium (yeast extract, peptone and dextrose). The suspension was diluted threefold to an OD of 2, equivalent to about $4 \times 10^{10}$ organism/ml, and then plated on solid YPD medium. The plates were then treated and read as described above.

Becton Dickinson blank discs (#31039) were used. The nonprotein amino acid and derivative compound solutions, at 0.5 M or 1.0 M, were tested by pipetting onto the discs in a volume of 25 microliters. The discs were placed on a plate comprising the organism. Inhibition of the growth of the following organisms (measured in mm zone of inhibition) at the following exemplary concentrations of exemplary compounds was observed, as shown in Table 3 below.

TABLE 3

*Staphylococcus aureus*

1-aminocyclopropane carboxylic acid (1M)

*Escherichia coli*

1-aminocyclopropane carboxylic acid (1M)
L-pyroglutamic acid (1M)
L-phenylalanine ethyl ester (1M)
L-tyrosine ethyl ester (1M)

*Saccharomyces cerevisiae* albizziin (2-amino-3-ureido-propionic acid) (0.5M)
L-α-amino-n-butyric acid (1M)
L-homoserine (1M) (2-amino-4-hydroxybutyric acid)
L-azetidine-2-carboxylic acid (1M)
L-phenylalanine ethyl ester (1M)
L-tryptophan ethyl ester (<1M)*
L-tyrosine ethyl ester (<1M)*

*Candida albicans* albizziin (2-amino-3-ureido-propionic acid) (0.5M)
L-phenylalanine ethyl ester (1M)
L-tryptophan ethyl ester (1M)

*sparingly soluble in water

Example 2
Inhibition of Microbial Growth by L-Pyroglutamic Acid

The ability of L-pyroglutamic acid (5-oxo-2-pyrrolidinecarboxylic acid) to inhibit the growth of *Staphylococcus aureus* was assessed.

*Staphylococcus aureus* was treated with L-pyroglutamic acid in water at a concentration of 3.8M, 2M, 1M, and 0.5M using the Kirby/Bauer disc diffusion method described in Example 1. A dose/response graph of zone of inhibition in millimeters vs. concentration in moles is shown in FIG. 1.

What is claimed is:

1. A method of inhibiting growth of *Staphylococcus aureus* in vitro, the method comprising applying to the site of the *Staphylococcus aureus* an effective amount of a compound selected from the group consisting of 1-aminocyclopropane carboxylic acid, and L-pyroglutamic acid (5-oxo-2-pyrrolidinecarboxylic acid), or a combination thereof.

2. A method of treating a *Staphylococcus aureus* infection in a human or animal in need thereof, the method comprising administering to the human or animal an effective amount of a compound selected from the group consisting of 1-aminocyclopropane carboxylic acid, and L-pyroglutamic acid (5-oxo-2-pyrrolidinecarboxylic acid), or a combination thereof.

3. The method of claim 2, wherein the method comprises administering the compound in a carrier.

4. The method of claim 2, wherein the method comprises administering the compound by a route selected from the group consisting of parenterally, orally, by inhalation and topically.

5. A method of inhibiting growth of *Escherichia coli* in vitro, the method comprising applying to the site of the *Escherichia coli* an effective amount of a compound selected from the group consisting of 1-aminocyclopropane carboxylic acid, L-pyroglutamic acid, L-phenylalanine ethyl ester, and L-tyrosine ethyl ester, or a combination thereof.

6. A method of treating a *Escherichia coli* infection in a human or animal in need thereof, the method comprising administering to the human or animal an effective amount of a compound selected from the group consisting of 1-aminocyclopropane carboxylic acid, L-pyroglutamic acid, L-phenylalanine ethyl ester, and L-tyrosine ethyl ester, or a combination thereof.

7. The method of claim 6, wherein the method comprises administering the compound in a carrier.

8. The method of claim 6, wherein the method comprises administering the compound by a route selected from the group consisting of parenterally, orally, by inhalation and topically.

9. A method of inhibiting growth of *Saccharomyces cerevisiae* in vitro, the method comprising applying to the site of the *Saccharomyces cerevisiae*, an effective amount of a compound selected from the group consisting of albizziin (2-amino-3-ureido-propionic acid), L-α-amino-n-butyric acid, L-homoserine (2-amino-4-hydroxybutyric acid), L-azetidine-2-carboxylic acid, L-phenylalanine ethyl ester, L-tryptophan ethyl ester, and L-tyrosine ethyl ester, or a combination thereof.

10. A method of treating a *Saccharomyces cerevisiae* infection in a human or animal in need thereof, the method comprising administering to the human or animal an effective amount of a compound selected from the group consisting of albizziin (2-amino-3-ureido-propionic acid), L-α-amino-n-butyric acid, L-homoserine (2-amino-4-hydroxybutyric acid), L-azetidine-2-carboxylic acid, L-phenylalanine ethyl ester, L-tryptophan ethyl ester, and L-tyrosine ethyl ester, or a combination thereof.

11. The method of claim 10, wherein the method comprises administering the compound in a carrier.

12. The method of claim 10, wherein the method comprises administering the compound by a route selected from the group consisting of parenterally, orally, by inhalation and topically.

13. A method of inhibiting growth of *Candida albicans* in vitro, the method comprising applying to the site of the *Candida albicans*, an effective amount of a compound selected from the group consisting of albizziin (2-amino-3-ureido-propionic acid), L-phenylalanine ethyl ester, and L-tryptophan ethyl ester, or a combination thereof.

14. A method of treating a *Candida albicans* infection in a human or animal in need thereof, the method comprising administering to the human or animal an effective amount of a compound selected from the group consisting of albizziin (2-amino-3-ureido-propionic acid), L-phenylalanine ethyl ester, and L-tryptophan ethyl ester, or a combination thereof.

15. The new method of claim 14, wherein the method comprises administering the compound in a carrier.

16. The method of claim 14, wherein the method comprises administering the compound by a route selected from the group consisting of parenterally, orally, by inhalation and topically.

\* \* \* \* \*